United States Patent [19]

Pegel

[11] 4,188,379

[45] Feb. 12, 1980

[54] STEROLINS AND THEIR USE

[75] Inventor: Karl H. Pegel, Durban Natal, South Africa

[73] Assignee: Roecar Holdings (Netherlands Antilles) N.V., Curacao, Netherlands Antilles

[21] Appl. No.: 843,496

[22] Filed: Oct. 19, 1977

[30] Foreign Application Priority Data

Dec. 30, 1976 [DE] Fed. Rep. of Germany ....... 2659466

[51] Int. Cl.² ..................... A61K 31/705; C07J 17/00
[52] U.S. Cl. ......................................... 424/182; 536/5
[58] Field of Search .......................... 536/5; 424/182

[56] References Cited

U.S. PATENT DOCUMENTS

| | | | |
|---|---|---|---|
| 3,933,789 | 1/1976 | Pegel | 536/5 |
| 3,966,918 | 6/1976 | Kawamata | 424/182 |
| 4,031,303 | 6/1977 | Murai et al. | 536/5 |

FOREIGN PATENT DOCUMENTS

| | | | |
|---|---|---|---|
| 1298047 | 4/1971 | United Kingdom | 536/5 |
| 1417272 | 12/1975 | United Kingdom | 536/5 |

Primary Examiner—Johnnie R. Brown
Assistant Examiner—Blondel Hazel
Attorney, Agent, or Firm—Cushman, Darby & Cushman

[57] ABSTRACT

Sterol glycosides and esters thereof with monocarboxylic acids of natural or synthetic origin are used to combat human and animal illness in dosages of not over 10 mg per day.

54 Claims, No Drawings

STEROLINS AND THEIR USE

BACKGROUND OF THE INVENTION

The invention is directed to sterolin compounds and their use for medicinal or therapeutic purposes.

Sterolins are compounds which occur frequently in nature in plants and microorganisms and their function in plants has not yet been established. Sterolins are glycosides of phytosterols including cholesterol and sterol type tetracyclic triterpenes as for example lanosterol and cycloartenol. About 100 different natural phytosterols have been found so far; of them many occur very rarely, as for example, lanosterol, while others occur frequently in plants but then only in small amounts as, for example, cycloartenol or cholesterol or some of them occur only in specific plants or plant families. However, several of these compound, also occur in various plants in relatively large amounts, as for example, sitosterol and campesterol as well as stigmasterol. Of these last mentioned compounds sitosterol particularly occurs most frequently.

The phytosterols correspond predominantly to the following general formula:

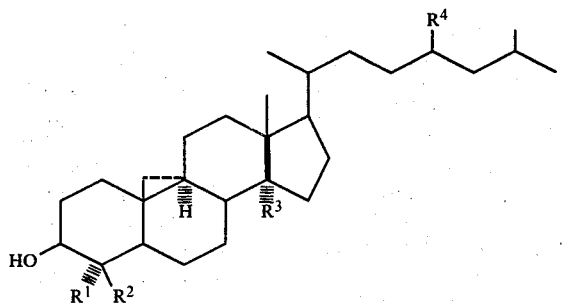

in which $R^1$, $R^2$ and $R^3$ are hydrogen atoms or methyl groups and in which $R^4$ can be a hydrogen atom or a methyl, ethyl, methylene or ethylidene group. Furthermore, double bonds can be present at various positions of the basic skeleton including the side chain.

It has already been established that these phytosterols are present in most plants as steryl glycosides, i.e., as sterolins and as their esters. An exception appears to be the tetracyclic triterpene sterols which do not seem to exist in nature as glycosides. The most common sterolins are monoglycosides, although a few diglycosides have been described. The most common sugar is D-glucose usually by means of which is joined to the sterol via the 3-β-hydroxy group, usually by means of an equatorial or β-glucoside bond. Other monosaccharides found in these compounds are mannose, galactose, arabinose and xylose. Sterolin esters are derived from monobasic carboxylic acids, e.g., palmitic acid.

Plants may contain specific sterols but usually they carry a mixture of different, sterols, sterol esters, sterolins and sterolin esters.

Sterols and sterol esters have not generally been used in medical practice except for specific phytosterols such as sitosterol and fucosterol which are employed; in very high doses of abnormally high serum cholesterol levels.

Sterolins and sterolin esters have already been described as biologically active. Reference to this is found in the German OS 21 13 215 and 23 12 285 corresponding to British patents 1,298,047 and 1,417,272. Furthermore, the German OS 23 03 247 and 21 13 215 corresponding to British patents 1,365,661 and 1,298,047 and the German OS 24 58 890 have disclosed the production of pharmaceutical specialities containing sterolin compounds. The entire disclosures of these German Inspection Applications and British patents are hereby incorporated by reference and they help to define the subject matter.

In these publications reference is made to the fact that sterolin compounds exhibit practically no toxicity and they can therefore be used in the treatment of various diseases. According to these publications, sterolins were also employed in the treatment of gout and arthritis.

Surprisingly and completely unexpected it has now been established that large doses of sterolins or sterolin esters may precipitate gout-like symptoms on predisposed patient.

SUMMARY OF THE INVENTION

According to this invention it is proposed to use sterolins and sterolin esters of natural semisynthetic or synthetic origin in treating human diseases in daily doses of less than 10 mg and preferably 0.03 to 0.75 mg/based on an assumed average human weight of 75 kg.

Since the phytosterol content in plant materials is usually much greater than the sterolin content, people and animals frequently do not receive enough sterolin and sterolin ester with their nourishment sterolin, so that their daily requirements are not reached. However, according to the invention sterolin enriched plant; extracts can also be used, where the added sterolin compounds are obtained by partial synthesis from natural starting products or by full synthesis either free (sterolins) or as esters (sterolin esters) with one more monocarboxylic acid derived ester group since these sterolin compounds are biologically active and have a special significance in maintaining the health of humans and animals. Unfortunately it has been established that while sterolins and their esters as they occur in plant materials and in sterolin enriched plant extracts are readily and rapidly absorbed and assimilated, no or little medicinal effect is obtained when crystalline or amorphous sterolin or sterolin ester aggregates are administered orally or parentally. It is absolutely necessary that the recommended therapeutics doses according to the invention make use of sterolins and/or sterolin esters to be included in a highly dispersed form. Processes for the production of such dispersions are described for example in the British patent 1,365,661 corresponding to the German OS 23 03 247 and in the German OS 24 58 890.

The above mentioned difficulties in the application of sterolins and their esters in regard to absorption and use are linked to their extreme insolubility in water. For example, 1 liter of water at room temperature dissolves only 9 mg of sitosterol-β-glucoside and 10 mg of cholesteryl-β-glucoside. In addition, all these compounds have only a very small lipid affinity and this explains the low activity or even lack of activity when sterolins are used by humans and/or animals in a particle size unsuitable for efficient absorption. It is therefore necessary requirement that the compounds to be used according to the invention are prepared or processed or incorporated into pharmaceutical products in such a manner that liquid or solid solutions, emulsions or solid dispersions are formed, by means of generally known and used principles and techniques such as adsorption, absorption or milling procedures with or without additives. These processes all aim at the comminution of the particles and reduction of crystallinity of the sterolins so that they are present as minute amorphous mono- or multimolecular aggregates in place of crystalline macroparticles. The compounds to be used according to the invention are mostly utilized with particle sizes of about 0.1 mm and smaller, and preferably of 0.06 mm and smaller.

The daily sterolin requirement with humans amounts to not less than 0.03 mg. However, in a certain cases this requirement may be substantially higher. The daily required amounts are administered in three or four equal doses per day. As mentioned above it has surprisingly been observed daily doses of more than 10 mg may possibly induce gout-like symptoms in predisposed patients although smaller doses of these particular compounds are used success successfully in the inflammatory treatment of manifestations such as arthritis and gout. The compounds are therefore usually employed at a daily total dosage of 0.45 mg given in three individual doses of 0.15 mg, preferably the total daily dose ranges between 0.30 to 0.75 mg given in three or four equal individual doses or as a single daily dose formulated to provide a gradual release of the active material. In the treatment of animal diseases required dose values can be calculated by using an average for human weight of 75 kg. The above values of the preferred dosages refer for sterolins, however, it has been established that sterolin esters are somewhat less effective and therefore somewhat higher daily and single doses are required. Nevertheless even these doses can be kept under a total daily amount of 10 mg without difficulty.

In addition, it has been found that a daily dose of less than 0.01 mg of sterol in compounds has no effect or scarcely any effect in treating various diseases and this indicates that the medicinally effective daily dose must amount to more than 0.01 mg. Fresh fruits and vegetables are not always available and the sterolin content in many processed plant products of various types has been reduced or is no longer present. In this case the compounds when used as described in the invention may be incorporated or added as a prophylactic precaution to food products considering the required amounts for humans.

The hypoglycemic activity of the sterolins has been described previously for sitosteryl glycoside by S. H. Ambike and M. R. R. Rao in Indian -Pharm., 29 (1967), 91–94. Further, in published patents and patent applications there is described the use of the compounds, particularly the sitosteryl glycosides, in the treatment of benign prostate hypertrophy and accompanying urogenital diseases, arthritis, hypercholesterolemia and arteriosclerosis, diseases due to increased uric acid levels, endocrine disturbances, and in geriatric conditions. Furthermore, the diuretic activity of sterolin and, the glycosides of sitosterol has already been described in the British patent 1,298,047 and confirmed by scientific investigations in "Indian J. Chem., 13 (1975), 199–200 ($\alpha$-sinasteryl-3-$\beta$-D-glucoside)." According to knowledge obtained so far as the compounds are useful in the treatment or assisting as an adjuvant in the treatment of the following diseases:

(A) Diseases of the gastro-intestinal tract and metabolic disturbances as follows:
(1) ulcers,
(B) Hormonal disturbances including those in the urogenital tract as follows:
(1) diseases of the urinary tract,
(2) benign prostate hypertrophy and complications related thereto, and
(C) diseases of the blood and blood forming organs:
(D) Diseases of the cardiovascular system as follows:
(1) In edematous conditions conditions, and
(E) Dermatological illnesses such as:
(1) dermatitis
(F) Diseases of the skeletal system and muscles such as:
(1) as anti inflammatory agents,
(2) Arthritic and rheumatic illnesses in general, and
(3) increased uric acid level.

However, in the treatment of these diseases, care should be taken that if not otherwise indicated sterolins and their esters, are used in doses not exceeding 10 mg per day.

The compositions can comprise, consist essentially of or consist of the materials set forth.

The invention will be further explained by means of the following examples.

DESCRIPTION OF THE PREFERRED EMBODIMENTS

EXAMPLE 1

Production of Sitosteryl-$\beta$-D-Glucoside

A mixture of 41.4 gram sitosterol and 55.2 gram of silver carbonate in toluene were heated at boiling temperature and distilled with stirring until the distillate passed over free of water. A solution of 82.2 gram acetobromglucose in 100 ml of toluene was then introduced dropwise into the stirred solution and boiled. While this addition proceeded toluene was continuously distilled so that the total amount of water formed in the reaction was removed azeotropically. The reaction vessel was protected from light during the reaction period. If necessary, the volume of the reaction mixture is held constant by addition of dry toluene. When addition of the acetobromglucose solution had been completed the reaction mixture was boiled until the distillate was water. The reaction mixture was then filtered hot free of and the residue washed with fresh hot toluene. The united filtrate and washing liquids were evaporated under reduced pressure and the residue was crystallized from ethanol or alternatively hexane can be used. The yield of sitosteryl glucoside tetraacetate was 22.4 gram, corresponding to a yield of 30%.

A solution 1 gram of sodium in 100 ml ethanol was added quickly with stirring to a solution of 10 gram sitosteryl glucoside tetraacetate in 600 ml ethanol at a temperature of 45° C. Stirring was continued for one hour before 2 liters water were added and the mixture was then stirred for another hour. The precipitated sitosteryl glucoside was filtered off and washed neutral with water prior to drying it for 12 hours in a vacuum. The yield was 6.9 gram, corresponding to 95%.

By selection of suitable starting compounds all the other mentioned sterolins can also be produced according to the above procedure.

EXAMPLE 2

Production of a Solid Solution of 24,25-Dihydrolanosteryl-$\beta$-D-Glucoside in Sitosterol and its incorporation into Lactose Granules In a solution of 100 gram sitosterol in 2000 ml of ethanol heated to reflux is dissolved 10 gram of 24,25-dihydrolanosteryl-$\beta$-D-glucoside. After complete solution of the sterolin the mixture is evaporated to dryness. The residue is milled or comminuted resulting in an amorphous powder with a particle size not exceeding 0.06 mm diameter.

The powder so obtained is slurried with 2 liters of water and intimately mixed with 3.2 kg of lactose. This mixture on drying results in the finished granulate product the preferred particle size is 0.7 to 1.2 mm diameter. This product is particularly well suited for the manufacturing of capsules having a content of 50 mg of the product, corresponding to a glucoside content of 0.15 mg.

Similarly granulates can be produced using the $\beta$-D-glucosides of sitosterol, stigmasterol, cholesterol and soya sterols.

The following generalisations apply when granulates of desired and required particle size are produced:

(a) The process can be used for all steryl glycosides and steryl glycoside esters.

(b) The sitosterol used as the solid diluent is as the most common and abundant phytosterol the sterol of phytosterol, although it is usually accompanied by similar sterols such as campesterol, stigmasterol and smaller amounts of less frequently occurring sterols such as brassicasterol, avenasterol and the like.

It has to be noted, however, that cholesterol and other sterols which do not have C-24 alkyl groups are not suitable as solid diluents or for solid solutions. These sterols can nevertheless be used as their corresponding sterolins.

(c) Other solvents can be used although is a relatively cheap solvent. Alternatively solvent mixtures may be employed. Other suitable solvents are, for example, methanol, chloroform, mixtures of methanol and chloroform, dioxane, acetone and other polar or non-polar useful solvents that are readily removed.

(d) Alternatively the lactose or any other suitable granulating agent can be slurried directly into the sterol-sterolin solution so that the steps of grinding micronizing the sterol-sterolin solid mixture and of preparing the aqueous slurry are eliminated. Alternatively the sterolin-sterol solid solution can be sprayed onto the carrier powder.

(e) In place of lactose other suitable carriers, such as, glucose, maltose, ascorbic acid, lecithin, starch, etc. may be used (f) In place of sitosterol or another acceptable sterol other suitable organic compounds can be used as solid diluents. Alternatively the sterolins can also be granulated without the use of micromized solid diluents.

(g) In order to produce the desired particle size then sterolin can also be comminuted by micronizing, grinding or by any other method to the desired particle size of preferably about 0.06 to 0.01 mm and especially not exceeding 0.1 mm, but certainly to such an extent that an almost complete loss of crystallinity is achieved before the sterolin is used as such or in a pharmaceutical preparation.

(h) Solid inert and insoluble or even soluble carriers can always be incorporated.

(i) The proportions of active and inactive compounds can be changed as required.

(j) The particle sizes within the above given limits as well as the granulate sizes and the method of production can be altered to suit requirements.

(k) At any production stage other pharmaceutically active compounds may be incorporated.

EXAMPLE 3

Production of Sitosteryl-$\beta$-D-Glucoside on Lactose as a Carrier

A solution of 12.5 gram of sitosteryl-$\beta$-D-glucoside in 750 ml methanol-chloroform (1 to 1) is prepared. This solution is intimately mixed with 500 grams lactose having a particle size not exceeding 0.15 mm. Subsequently, the solvent is removed in a vacuum. The mixture of sterolin and lactose (1:40) is dried for 12 hours in a vacuum oven at 60° C. The dried product is pulverized so that the particle size does not exceed 0.15 mm. This powder can then be incorporated into various pharmaceutical products.

The solvent employed in this process or components of solvent mixture can be changed so that, example, pure ethanol, methanol, or chloroform or various mixtures of these solvents are used. The ratio of sterolin and lactose can also be changed. In addition other sterolins such as soy steryl glucosides, chloresteryl glucoside or stigmasteryl glucoside or different inert carriers such as glucose, ascorbic acid or starch may be used. The powdered, impregnated lactose or other powdered sterolin impregnated carriers can be granulated for encapsulation or they may be processed differently for incorporation into pharmaceutical products. Other pharmaceutically active compounds can be added together with the sterolins in the production of the impregnated powder.

EXAMPLE 4

Production of Tablets Containing of Stigmasteryl-$\beta$-D-Glucoside

In a reflexing solution of 2 liter of a chloroform-methanol mixture (1 to 3) and containing 100 gram soya bean sterols (sitosterol:campesterol:stigmasterol approximating 60:30:10) is dissolved 10 grams of stigmasteryl glucoside. This solution is evaporated to dryness and the residue micronized or otherwise comminuted until a predominantly amorphous product results with a particle size not exceeding 0.06 mm. This product is then mixed with accepted tabletting aids before it is processed by means of the usual techniques into normal or slow-release tablets having a content of 0.15 mg stigmasteryl-$\beta$-D-glucoside per tablet.

The modifications (a) to (k) mentioned in Example 2 apply also here.

Production of Dragees

A solution of 630 mg of sitosteryl-$\beta$-D-glucoside in 2.5 liter ethanol is intimately mixed with 2500 grams lactose and the mixture dried under a vacuum at 45° C. The impregnated lactose is thoroughly mixed with 450 gram sucrose (both lactose and sucrose should not have a particle size exceeding 0.15 mm) and this mixture is granulated with a solution of 50 gram gelatin in 2.3 liter water. The granulate formed is dried under a reduced pressure at 45° C. and is then intimately mixed with 13 gram magnesium stearate. The finished mixture (3013 gram) is molded into about 4000 kernels which are subsequently given a dragee coating covering which may be suitably suitably colored. Each dragee contains 0.15 mg sitosteryl-$\beta$-D-glucoside, 595.28 mg lactose, 107.143 mg sucrose, 11.905 mg gelatin and 3.095 mg magnesium stearate. Similarly, soya steryl-$\beta$-D-glucoside, tall oil steryl-$\beta$-D-glucoside, cholesterol-$\beta$-D- glucoside, stigmasterol-β-D-glucoside and sitosterol-β-D-galactoside were molded to dragee kernels.

Production of an Ointment Containing 0.25% Cholesteryl-β-D-Glucoside

An amount of 2.5 gram chloesteryl-β-D-glucoside is worked into 90 gram emulsifying cetyl-stearyl alcohol. The mixture, after addition of 105 gram viscous paraffin and 105 grams white Vaseline (petroleum jelly) is melted on the water bath at 60° C. Into this molten mixture is stirred in small portions 697.5 gram water of about the same temperature and the complete mixture is then allowed to cool with constant stirring.

Production of a Cream Containing 0.25% Soya Steryl-glucoside

An amount of soya steryl-β-D-glucoside is introduced into 500 gram wool wax alcohol and heated on the water bath to about 50° C. The fluid mixture is then treated in small portions with 497.5 gram water kept at about the same temperature on completion of water addition. The cream is allowed to cool with constant stirring and if necessary addition of water to replenish evaporation losses.

EXAMPLE 4A

Production of Pharmaceutically Acceptable Solutions (a) Solution Containing Semisynthetic Soya Steryl-β-D-Glucoside A solution of 10 gram polyvinyl pyrrolidone in 4 liter distilled water at a temperature of 65° C. is added to a boiling solution of 600 mg semisynthetic soya steryl B-D glucoside in 6 liter absolute ethanol. The cooled 60% ethanolic solution is transferred into 250 ml flasks. The patients were instructed to take one-half teaspoon corresponding to 2.5 ml of this mixture 3 times per day.

The prepared solution provides forty 250 ml flasks, each of which holds about 100 doses of 2.5 ml this being sufficient for a treatment of about 33 days. Each teaspoon 2.5 ml provides of 0.15 mg sterolins, 2.5 mg PVP and 1.5 ml ethanol.

Care must be taken not to exceed concentrations of over 7.5 mg of sterolins and 100 mg of PVP for each 100 ml of 60% aqueous ethanol if clouding of solutions is to be avoided, i.e., about 0.1875 mg of sterolins per 2.5 ml of aqueous 60% ethanol is the maximum dose for a clear solution.

According to the described process there can also solutions of other steryl monoglycosides or monoglucosides can be prepared. However, since all these compounds have low solubilities their solutions prepared as described above, should not be subjected to low temperatures in order to avoid turbidity.

(b) Solutions Containing Semisynthetic Sitosteryl-β-D-Maltoside

An amount of 800 mg sitosteryl-β-D-maltoside is dissolved in a mixture of 3 liter ethanol and 7 liters of water under gentle reflux. The cooled 30% aqueous ethanol solution is transferred into 250 ml flasks. The patients were instructed to take 2.5 ml of this solution 3 times per day (depending on its volume either of one-half or an entire teaspoon full).

The entire solution provided forty 250 ml flasks, each holding about 100 doses of 2.5 ml, this being sufficient for a treatment period of about 33 days. One dose of 2.5 ml of the solution contains 0.2 mg sterolins and 0.75 ml of ethanol.

According to the described process solutions of other sterol disaccharides can be prepared. The water solubility of β-D-maltoside, β-D-lactoside, and β-D-cellobioside of sitosterol are respectively 0.38 mg, 0.21 mg and 0.75 mg per ml water 24° C. This solubility is above the preferred individual doses employed for the compounds.

The preferred individual dose employed for steryl disaccharides is 0.2 mg, therefore 0.6 mg per day.

It has to be pointed out that other pharmaceutically effective compounds can be incorporated into the solutions of the steryl disaccharides. Furthermore, the alcohol content of these sterolin solutions can be altered alternatively; other pharmaceutically acceptable solvents can be used. Furthermore, pure water can be made use of as the sole solvent.

EXAMPLE 5

Pharmacological Testing of Sterolins (a) Toxicity Investigation of Sterolins

In toxicity trials with rats, mice, rabbits, dogs and primates by oral administration of, e.g., sitosteryl-β-D-glucoside with doses of b 1 to 2 gram/kg of body weight no toxic effects were observed. Also, when administration was carried out over a long period with daily doses of 100 to 200 mg/kg of body weight no toxic or gout-like effects could with these animal species be detected appearances so that the tolerance can be designated as good.

(b) Investigation of the Anti Inflammation Effect of Sterol Glycosides (1) Steralins produced from tall oil sterols containing about 99.5% of total sterols with 95% sitosterol and 4% campesterol were used. This sterol in mixture was slurried with gum arabic to provide suspension of concentrations which permitted administration of 1.0 ml per 100 grams of body weight.

The inflammatory agent, in this case freeze dried active baker's yeast, was made up as a 2% suspension in sterile physiological salt solution (0.9% NaCl). A volume of 0.1 ml of this yeast suspension was injected in each case into plantar area the of the right hind paw of the test animals. The test animals had been pretreated by forced feeding with the talloil sterol derived sitosteryl glucoside at three intervals namely, 48, 24 and one hour before the injection of the inflammatory agent. The micronized amorphous sterolin glucoside having a particle size of not exceeding 0.06 mm was fed in doses of 500 or 1000 mg/kg body weight the different test groups, each consisting of 24 male rats with an average weight of about 230 grams.

Half of the animals of each group were killed after 5 hours in order to establish the acute inflammation, the remaining half was investigated after 24 hours to determine the residual inflammation. The edema arising in the right hind paw was compared by weight with the left hind paw as control into which only a sterile salt solution (0.9% NaCl) had been injected. The average change in the foot weight of each treated group was compared with that of a control group of animals which in place of the test material received the aqueous gum arabic solution at a rate of 0.1 ml/100 grams of body weight.

The average reduction of inflammatory reaction is seen from the following table:

| Dose mg/kg oral (48, 24 and 1 hour before administration of the yeast) | Average Percentage Reduction of the Rat Paw Edema | |
|---|---|---|
| | After 5 hours | After 24 hours |
| 500 | 11.2 | 17.6 |
| 1000 | 14.4 | 20.3 |

Similarly, other sterolins were investigated. In these cases doses of 500 mg/kg body weight suspended, in a solution were administered gum arabic 24 and one hour before the dispensing delivery of the anti-inflammation releasing agent (in the case of the compounds 1 to 5 suspensions of 2% baker's yeast in physiological saline solution and with the substances 6 to 8 suspensions of 3½% baker's yeast in physiological saline solution were administered).

The results are given in the following table:

| Substance | Average Percentage Reduction of the Rat Paw Edema | |
|---|---|---|
| | After 5 hours | After 24 hours |
| (1) cholestanyl-$\beta$-D-glucoside | 7.7 | 11.1 |
| (2) lanosteryl-$\beta$-D-glucoside | 1.8 | 3.8 |
| (3) stigmasteryl-$\beta$-glucoside | 3.2 | 8.7 |
| (4) ergosteryl-$\beta$-glucoside | 6.8 | 14.3 |
| (5) sitosteryl-$\beta$-glucoside | 10.4 | 10.8 |
| (6) sitosteryl-$\beta$-glucoside | 7.8 | 12.3 |
| (7) sitosteryl-$\beta$-glucoside | 12.3 | 10.4 |
| (8) sitosteryl-$\beta$-glucoside | 14.3 | 12.7 |

EXAMPLE 6

Patients with various manifestations of chronic gout were treated daily over a time span of 6 months with 3 capsules, each containing 0.15 mg sitosteryl-$\beta$-D-glucoside, one before each main meal. Even after the first month of treatment none of the patients suffered any deterioration in their condition.

These properties have not been observed for the customary and frequently used agents. The treatment of so-called acute arthritic gout is normally initiated through rest and by administering anti-inflammation agents. In addition simultaneously the specific anti-gout agents are administered. The most common anti-inflammatory agents included for example, acetylsalicylic acid, indomethacin, phenylbutazone, ibuprofen, fluphenamic acid, oxyphenbutazone, ketoprofen, chloroquine and the sodium salt of diclophenic acid.

Acetylsalicylic acid is given as an antiphlogistic agent in daily doses of about 300 to 1000 mg and in the treatment of gout experimentally in doses of 5000 to 10,000 mg. Although the compound has relatively few side effects, those that do occur are feared because of their severity, as for example, in the occurrence of agranulocytosis.

Phenylbutazone is dispensed in daily doses of about 100 to 300 mg and is known for its relatively severe side effects which can for example, manifest themselves in stomach, intestinal, liver-and renal diseases, thrombopathias, hemolytic anemias and ulcers of the stomach and small intestine whereby the latter are frequently promoted by these compounds, remain latent and may erupt on further medication. For these reasons the use of phenyl butazone is limited to about 7 days to one month and continuous supervision of the condition of health by a physician is required. Although Indomethacin has fewer side effects than phenylbutazone this compound must also be taken in daily in doses of about 25 to 200 mg over longer periods. Similarly ibuprofen has fewer side effects than phenyl butazone, but it must be taken over longer periods in daily doses of up to 1200 mg.

Similar side effects induced by phenyl butazone are also caused by oxyphenbutazone which is given in daily doses of about 200–300 mg. Fluphenamic acid given customary daily doses of about 600 mg, likewise can also initiate side effects by likewise causing deteriorations in the condition of ulcers in the stomach and small intestine. Side effects similar to those caused by ibuprofen are also frequently induced by ketoprofen which is given in daily amounts of about 150 mg, while chloroquine in daily doses of about 250 mg can cause hemolytic anemia in predisposed persons. Also, the sodium salt of diclophenic acid given in daily quantities of up to 75 mg can cause changes in the blood count.

Always the agents used for their effectiveness against gout sulfinpyrazone is administered daily in amounts of 300–400 mg with possible side effects such as aggravation of existing ulcers and changes in the blood composition. Probenecid given in initial daily doses of 500 mg can liberate the induce formation of urate stones at the initial dosage of 500 mg. Allopurinol usually administered in daily doses of 300 mg acts as pyrimidine antagonist and can therefore not be given during pregnancy and lactation and it can initiate the typical side effects produced by pyrimidine antagonists. Benzobromarone given in usual dosage of 100 mg per day cannot be administered in the presence of severe kidney function disturbances, but otherwise other marked side effects have not yet been reported.

Colchicine which has a high toxicity is only used for reducing acute attacks of gout.

On the other hand, the compounds of the invention are administered in daily doses of about 0.03 to 0.75 mg and preferably 0.15 to 0.45 mg. Although the response to the medication requires sometime about 7 to 30 days, it is nevertheless balanced and continuous. However, unexpectedly and in contrast to the previous publications very high doses of the sterolins can induce hyper reaction in the form of gout-like attacks in predisposed persons, although the very same compounds in smaller doses are excellent agents for the treatment of gout. An explanation for this behavior is that the compounds probably flush out uric acid and at very high doses they therefore cause gout-like appearances. This side effect, however, gradually disappears after a few days on termination, or reducing dose administration.

In order to avoid this adverse reaction the daily dose according to the invention is limited to below 10 mg since at smaller doses no gout-like attacks are induced in predisposed persons.

The compounds of the invention are administered in doses which are smaller by a factor of $10^{-2}$ to $10^{-3}$ below the present day accepted pharmaceutical compounds.

EXAMPLE 7

Clinical Investigations of Effect in the Treatment of Benign Prostate Hypertroph In the clinical trials capsules were dispensed 3 times a day one before each main meal and each capsule containing 0.15 mg sitosteryl-$\beta$-D-glycoside. Alternately solutions according to Example 4A were used. The patients received 3×30 drops of the solutions daily after meal times.

In all, over 1,100 patients were treated with these preparations their ages ranging between 52 and 89 years. The average age of the patients was 69 years.

In part the preparations were prescribed in combination with antibiotics, sulfonamides, furantoins or heart and circulatory agents. An exceptionally good tolerance was observed when these combination prescriptions were given (no adverse reactoons have yet been reported).

In general duration of the treatment extended over several months; in several instances treatment lasted over 1½ years. Already after 14 days the patients consistently showed a definite subjective improvement.

Objectively the following could be established:

(a) Residual Amounts of Urine (1) Residual amounts of urine up to 100 ml disappeared completely in 100% of the cases.

(2) Residual amounts of urine between 100 and 200 ml disappeared completely in about 90% of the cases.

(3) Residual amounts of urine, between 200 and 500 ml, disappeared in 72% of the trial group. Residual amounts of 100 ml of urine are retained by 10% of this group of patients while, the remainder had to undergo an operation or electroresectionation.

(b) Size of the Prostate

In 1150 cases the gland size had definitely been reduced according to the of rectalfinger probe test.

In objective measurements of the colliculus sphincter distance established no changes in only 4% of the investigated cases. On the average an internal reduction of about 0.6 to 0.8 cm. was delivered. In many cases the sphincter distance was reduced from 4.2 to 3.2 cm, in several patients from 3.2 to 2.4 cm and in others from 3.0 to 2.0 cm.

(c) Bladder Pressure

In 88% of the manometrically tested patients an increase of the mictation pressure was absent during treatment with the preparation(s). Initial low values of 40-60 mm Hg increased after a treatment period of 3 months to 80-100 mm Hg. In general the resistance pressure was reduced from about 10 to 20 mm Hg. In only 12% of the treated patients no change of the bladder pressure value could be detected, however there was no further deterioration in the parameters investigated.

(d) Microscopic Urine Examination

An improvement in the urine condition was also indicated by a decline of the number of leucocytes in the sediment. The huge to large numbers of leucocytes, present before the treatment decreased gradually during the course of treatment and only isolated leucocytes were detected during the final examination at the end of the treatment.

A reduction of the number of leucocytes was obtained in 96% of all cases.

In 863 patients (approximately, 70% of all cases) in which the urine infection was produced by Coli or Proteus bacteria, cultures were sterile at the end of the treatment period. In 156 patients (about 13%) these remarkable results were not achieved, but a clear improvement of the bacteriological condition, was obtained in that only isolated micro organisms were still detectable at the end of the trial period. The remainder of the infections were caused by Pyocyaneus infections and they could not be influenced by the medication. These results do not, however, imply that the compounds have anti-bacterial activity.

In no case could a deterioration of the sediment or bacteriological condition be established.

(e) X-ray Controls

Discharge obstruction in patients caused by the enlarged prostate at the neck of the bladder results in residual urine accumulation right to the upper urinary tract resulting in a dilation of the urethra of urinary tract, the renal pelvis and the cups. This may be demonstrated by means of X-ray methods. In theory these dilations normalize when the obstruction at the neck of the bladder disappears. In many cases this normalization is easily observed on corresponding X-ray pictures. In 72 patients the interpretation of the X-ray pictures indicated that dilations of the upper uninary tract due to the obstruction at the neck of the bladder caused by an enlarged prostate, had been clearly reduced. In several cases a noticeable reduction was observed within 4 to 6 weeks. In the majority of the cases a three month treatment was necessary in order to detect retrogression of the dilation of the urethra by the X-ray method. In no cases could a deterioration in the initial condition be detected.

EXAMPLE 8

Clinical Trial for the Effectiveness in Arthritis, and related disorders

Patients with and various rheumatic disorders were treated with an average of 3 capsules, each with 0.15 mg of sitosteryl-$\beta$-D-glucoside per day.

A definite reduction in the inflammatory condition was noticed. Because of the subjective freedom from pain and the detected objective reduction of inflammatory appearances even in patients who had received supplementary adrenal hormones for years for their cortisone treatment could be reduced or even stopped. Similarly the administration of so-called symptomatic antirheumatics could be withdrawn in most treated patients.

What is claimed is:

1. A composition suitable for administration as an anti-inflammatory, gout-combatting or prostate hypertrophy combatting agent comprising a sterol glycoside or ester thereof together with a pharmaceutically acceptable carrier in dosage form, said dosage containing 0.1 to 0.75 mg of said sterol, said sterol being tall oil sterols glucosides, sitosterol glucoside, ergosterol glucoside, lanosterol glucoside, 24,25-dihydrolanosterol glucoside, stigmasterol glucoside, soya sterol glucosides, sitosterol-$\beta$-D-galactoside, sitosterol-$\beta$-D-maltoside, sitosterol-$\beta$-D-lactoside or sitosterol-$\beta$-D-cellobioside.

2. A composition according to claim 1 containing 0.1 to 0.25 mg of said sterol.

3. A composition according to claim 2 containing 0.15 mg of said sterol.

4. A composition according to claim 1 containing 0.45 mg of said sterol.

5. A composition according to claim 1 including polyvinyl pyrrolidone.

6. In a process of treating a human illness which is an inflammatory illness and which is susceptible to treatment by a sterol glycoside or ester thereof comprising administering to a patient as a dosage an effective amount to treat said illness of a sterol glycoside or ester thereof with a monocarboxylic acid, said amount being 0.30 to not over 0.75 mg per day, the minimum individual dosage being 0.075 mg, said sterol being tall oil sterols glucosides, sitosterol glucoside, ergosterol glucoside, lanosterol glucoside, 24,25-dihydrolanosterol glucoside, stigmasterol glucoside, soya sterol glucosides, sitosterol-β-D-galactoside, sitosterol-β-D-maltoside, sitosterol-β-D-lactoside or sitosterol-β-D-cellobioside.

7. A process according to claim 6 wherein the daily dose is 0.45 mg and the individual dose is 0.15 mg.

8. A process according to claim 6 wherein there are administered four individual dosages per day of 0.15 mg each.

9. A process according to claim 6 wherein the minimum individual dosage is 0.10 to 0.25 mg.

10. A process according to claim 6 wherein the minimum individual dosage is 0.1 mg.

11. A process according to claim 6 wherein the sterol is sitosterol-β-D-glucoside.

12. A process according to claim 11 wherein the daily dose is 0.30 to 0.45 mg per day.

13. A process according to claim 12 wherein there are administered 3 to 4 doses a day.

14. A process according to claim 13 wherein there are administered three doses a day and the minimum individual dose is 0.10 mg.

15. A process according to claim 6 wherein there is employed a glucoside of tall oil sterols, sitosterol, ergosterol, lanosterol, 24,25-dihydrolanosterol, stigmasterol or soya sterols.

16. A process according to claim 6 wherein there is employed a β-d-galactoside, β-D-maltoside, β-D-lactoside β-D-glucoside or β-D-cellobioside of sitosterol.

17. A process according to claim 6 of combatting arthritis comprising administering to a patient having arthritis an arthritic combatting sterol glycoside.

18. A process according to claim 6 wherein the daily dose is 0.45 mg.

19. A process according to claim 6 wherein the sterol glycoside or ester thereof is employed as a solid wherein most of the particles have a size below 0.1 mm in diameter.

20. A process according to claim 19 wherein most of the particles have a diameter below 0.06 mm.

21. A process according to claim 6 wherein the sterol glycoside or ester thereof is administered in liquid form.

22. In a process of treating a human illness which is gout, and which is susceptible to treatment by a sterol glycoside or ester thereof comprising administering to a patient as a dosage an effective amount to treat said illness of a sterol glycoside or ester thereof with a monocarboxylic acid, said amount being 0.30 to not over 0.75 mg, per day, the minimum individual dosage being 0.075 mg, said sterol being tall oil sterols glucoside, istosterol glucoside, ergosterol glucoside, lanosterol glucoside, 24,25-dihydrolanosterol glucoside, stigmasterol glucoside, soya sterol glucoside, sitosterol-β-D-galactoside, sitosterol-β-D-maltoside, sitosterol-β-D-lactoside or sitosterol-β-D-cellobioside.

23. A process according to claim 22 wherein the minimum individual dosage is 0.10 to 0.25 mg.

24. A process according to claim 22 wherein the minimum individual dosage is 0.1 mg.

25. A process according to claim 22 wherein the sterol is sitosterol-β-D-glucoside.

26. A process according to claim 25 wherein the daily dose is 0.30 to 0.45 mg per day.

27. A process according to claim 26 wherein there are administered 3 to 4 doses a day.

28. A process according to claim 27 wherein there are administered three doses a day and the minimum individual dose is 0.10 mg.

29. A process according to claim 22 wherein there is employed a glucoside of tall oil sterols, sitosterol, ergosterol, lanosterol, 24,25-dihydrolanosterol, stigmasterol or soya sterols.

30. A process according to claim 22 wherein there is employed a β-D-galactoside, β-D-maltoside, β-D-lactoside, β-D-glucoside or β-D-cellobioside of sitosterol.

31. A process according to claim 22 wherein the daily dose is 0.45 mg.

32. A process according to claim 22 wherein the sterol glycoside or ester thereof is employed as a solid wherein most of the particles have a size below 0.1 mm in diameter.

33. A process according to claim 22 wherein most of the particles have a diameter below 0.06 mm.

34. A process according to claim 22 wherein the sterol glycoside or ester thereof is administered in liquid form.

35. A process according to claim 22 wherein the daily dose is 0.45 mg and the individual dose is 0.15 mg.

36. A process according to claim 22 wherein there are administered four individual dosages per day of 0.15 mg. each.

37. In a process of treating a human illness which is prostate hypertrophy and which is susceptible to treatment by a sterol glycoside or ester thereof comprising administering to a patient as a dosage an effective amount to treat said illness of a sterol glycoside or ester thereof with a monocarboxylic acid, said amount being 0.30 to not over 0.75 mg per day, the minimum inividual dosage being 0.075 mg, said sterol being tall oil sterols glucosides, sitosterol glucoside, ergosterol glucoside, lanosterol glucoside, 24,25-dihydrolanosterol glucoside, stigmasterol glucoside, soya sterol glucosides, sitosterol-β-D-galactoside, sitosterol-β-D-maltoside, sitosterol-β-D-lactoside or sitosterol -β-D-cellobioside.

38. A process according to claim 37 wherein the daily dose is 0.45 mg and the individual dose is 0.15 mg.

39. A process according to claim 37 wherein there are administered four individual dosages per day of 0.15 mg each.

40. A process according to claim 37 wherein the minimum individual dosage is 0.10 to 0.25 mg.

41. A process according to claim 37 wherein the minimum individual dosage is 0.1 mg.

42. A process according to claim 37 wherein the sterol is sitosterol-β- -D-glucoside.

43. A process according to claim 42 wherein the daily dose is 0.30 to 0.45 mg per day.

44. A process according to claim 43 wherein there are administered 3 to 4 doses a day.

45. A process according to claim 44 wherein there are administered three doses a day and the minimum individual dose is 0.10 mg.

46. A process according to claim 42 wherein the doses are administered to a patient having prostate hypertrophy.

47. A process according to claim 43 wherein the total daily doses is 0.30 to 0.45 mg per day.

48. A process according to claim 47 wherein there are administered 3 to 4 doses a day.

49. A process according to claim 37 wherein there is employed a glucoside of tall oil sterols, sitosterol, ergosterol, lanosterol, 24,25-dihydrolanosterol, stigmasterol or soya sterols.

50. A process according to claim 37 wherein there is employed a β-D-galactoside, β-D-maltoside, β-D-lactoside, β-D-glucoside or β-D-cellobioside of sitosterol.

51. A process according to claim 37 wherein the daily dose is 0.45 mg.

52. A process according to claim 37 wherein the sterol glycoside or ester thereof is employed as a solid wherein most of the particles have a size below 0.1 mm in diameter.

53. A process according to claim 52 wherein most of the particles have a diameter below 0.06 mm.

54. A process according to claim 37 wherein the sterol glycoside or ester thereof is administered in liquid form.

* * * * *